United States Patent
Pazenok et al.

(10) Patent No.: US 10,273,215 B2
(45) Date of Patent: Apr. 30, 2019

(54) PROCESS FOR PREPARING SUBSTITUTED PYRAZOLES CONTAINING HALOALKOXY- AND HALOALKYLTHIO GROUPS FROM ALPHA,ALPHA -DIHALOALKYLAMINES AND KETIMINES

(71) Applicants: Bayer CropScience Aktiengesellschaft, Monheim am Rhein (DE); CENTRE NATIONAL DE LA RECHERCHE SCIENTIFIQUE, Paris (FR)

(72) Inventors: Sergii Pazenok, Solingen (DE); Jean-Pierre Vors, Sainte Foy les Lyon (FR); Frédéric R. Leroux, Herrlisheim (FR); Etienne Schmitt, Strasbourg (FR)

(73) Assignees: BAYER CROPSCIENCE AKTIENGESELLSCHAFT, Monheim am Rhein (DE); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 0 days.

(21) Appl. No.: 15/738,470

(22) PCT Filed: Jun. 21, 2016

(86) PCT No.: PCT/EP2016/064320
§ 371 (c)(1),
(2) Date: Dec. 20, 2017

(87) PCT Pub. No.: WO2016/207167
PCT Pub. Date: Dec. 29, 2016

(65) Prior Publication Data
US 2018/0186749 A1    Jul. 5, 2018

(30) Foreign Application Priority Data
Jun. 26, 2015  (EP) .................................... 15290166

(51) Int. Cl.
| | | |
|---|---|---|
| C07D 231/16 | (2006.01) | |
| C07C 251/08 | (2006.01) | |
| C07C 251/12 | (2006.01) | |
| C07C 251/30 | (2006.01) | |
| C07C 251/26 | (2006.01) | |

(52) U.S. Cl.
CPC .......... *C07D 231/16* (2013.01); *C07C 251/08* (2013.01); *C07C 251/12* (2013.01); *C07C 251/26* (2013.01); *C07C 251/30* (2013.01)

(58) Field of Classification Search
None
See application file for complete search history.

(56) References Cited

U.S. PATENT DOCUMENTS

| | | |
|---|---|---|
| 7,329,633 B2 | 2/2008 | Dunkel et al. |
| 7,358,387 B2 | 4/2008 | Lantzsch et al. |
| 7,939,673 B2 | 5/2011 | Pazenok et al. |
| 8,350,053 B2 | 1/2013 | Pazenok et al. |
| 8,629,288 B2 | 1/2014 | Pazenok et al. |
| 9,145,370 B2 * | 9/2015 | Pazenok .............. C07D 231/14 |
| 2010/0274049 A1 | 10/2010 | Lui et al. |

FOREIGN PATENT DOCUMENTS

| | | |
|---|---|---|
| EP | 2072497 | 6/2009 |
| EP | 2057126 | 11/2010 |
| EP | 2628722 | 8/2013 |
| EP | 2890682 | 6/2016 |
| EP | 2809653 | 8/2017 |
| WO | WO-2003/070705 | 8/2003 |
| WO | WO-2005/042468 | 5/2005 |
| WO | WO-2008/013925 | 1/2008 |
| WO | WO-2008/022777 | 2/2008 |
| WO | WO-2009/028727 | 3/2009 |
| WO | WO-2009/106230 | 9/2009 |
| WO | WO-2009/112157 | 9/2009 |
| WO | WO-2012/025557 | 3/2012 |
| WO | WO-2013/113829 | 8/2013 |
| WO | WO-2014/033164 | 3/2014 |

OTHER PUBLICATIONS

European Search Report dated Sep. 2, 2015, for European Application No. 15290166.6-1462, filed on Jun. 26, 2015,12 pages.
Gulevich, A. et al. (2008), "The Ugi reaction with $CF_3$-carbonyl compounds: effective synthesis of α-trifluoromethyl amino acid derivatives," *Tetrahedron* 64:11706-11712.
International Search Report dated Jul. 26, 2016, for International Application No. PCT/EP2016/064320, filed on Jun. 21, 2016, 4 pages.
Kenis, S. et al. (2011), "Straightforward synthesis of 1-alkyl-2-(trifluoromethyl)aziridines starting from 1,1,1-trifluoroacetone," *Org. Biomol. Chem.*, 9:7217-7223.
Kirsch, P. et al. (2006), "A Convenient Synthetic Route to Tetrahydropyran-Based Liquid Crystals," *Eur. J. Org. Chem.*, 326-3331.
Pashkevich et al. (1981), "3,5-Bis(fluoroalkyl)pyrazoles by reacting bisperfluoroalkyl diketones with hydrazines," *Union Chemical Society Journal*, 26(1):105-107.
Perrone, S. et al. (2013), "Synthesis and reactivity of trifluoromethyl substituted oxaziridines," *Tetrahedron*, 69:3878-3884.
Vanden Heuvel, W. et al. (1964), "Characterization and Separation of Amines by Gas Chromatography," *American Chemical Society*, 36(8):1550-1560.

\* cited by examiner

*Primary Examiner* — Kamal A Saeed
(74) *Attorney, Agent, or Firm* — Morrison & Foerster LLP

(57) ABSTRACT

The present invention relates to a novel process for preparing 3,5-bis substituted pyrazoles containing haloalkoxy- and haloalkylthio groups.

6 Claims, No Drawings

PROCESS FOR PREPARING SUBSTITUTED PYRAZOLES CONTAINING HALOALKOXY- AND HALOALKYLTHIO GROUPS FROM ALPHA,ALPHA -DIHALOALKYLAMINES AND KETIMINES

CROSS REFERENCE TO RELATED APPLICATIONS

This application is a National Phase application under 35 U.S.C. § 371 of International Application No. PCT/EP2016/064320, filed Jun. 21, 2016, which claims priority benefit of European Application No. 15290166.6, filed Jun. 26, 2015.

The present invention relates to a novel process for preparing 3,5-bis substituted pyrazoles containing haloalkoxy- and haloalkylthio groups.

Polyfluoroalkylpyrazolylcarboxylic acid derivatives and 3,5-bis(haloalkyl)pyrazoles are valuable precursors of active fungicidal ingredients (WO 2003/070705, WO 2008/013925, WO 2012/025557).

Pyrazolecarboxylic acid derivatives are typically prepared by reacting acrylic acid derivatives having two leaving groups with hydrazines (WO 2009/112157 and WO 2009/106230). WO 2005/042468 discloses a process for preparing 2-dihaloacyl-3-aminoacrylic esters by reacting acid halides with dialkylaminoacrylic esters and subsequent cyclization thereof with alkyl hydrazines. WO 2008/022777 describes a process for preparing 3-dihalomethylpyrazole-4-carboxylic acid derivatives by reacting α,α-difluoroalkylamines in the presence of Lewis acids with acrylic acid derivatives and subsequent reaction thereof with alkylhydrazines.

3,5-bis(fluoroalkyl)pyrazoles are prepared by reacting bisperfluoroalkyl diketones (e.g. 1,1,1,5,5,5-hexafluoroacetylacetone) with hydrazines (cf. Pashkevich et al., Zhurnal Vsesoyuznogo Khimicheskogo Obshchestva im. D. I. Mendeleeva (1981), 26(1), 105-7), the yield being only 27-40%. The synthesis, isolation and purification of the polyfluoroalkyl diketones is very complex since the compounds are generally very volatile and highly toxic.

In the light of the prior art described above, it is an object of the present invention to provide a process that does not have the aforementioned disadvantages and hence gives a route to 3,5-bis(haloalkyl)pyrazole derivatives in high yields.

The object described above was achieved by a process for preparing 3,5-bis(haloalkyl)pyrazoles of the formula (Ia) and (Ib),

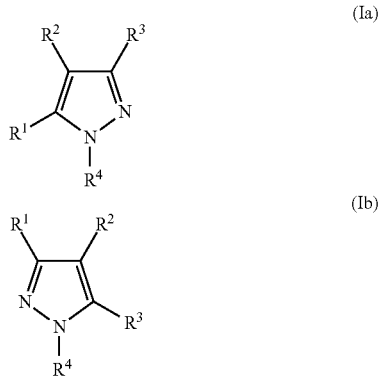

in which
$R^1$ is selected from $C_1$-$C_6$-haloalkyl-ethers or $C_1$-$C_6$-haloalkyl-thioethers;
$R^2$ is selected from H, halogen, COOH, (C=O)O$R^5$, CN and (C=O)N$R^6R^7$;
$R^3$ are each independently selected from $C_1$-$C_6$-haloalkyl alkyl;
$R^4$ is selected from H, $C_1$-$C_8$ alkyl, aryl, pyridyl;
$R^5$ is selected from $C_{1-12}$-alkyl, $C_{3-8}$-cycloalkyl, $C_{6-18}$-aryl, $C_{7-19}$-arylalkyl and $C_{7-19}$-alkylaryl;
$R^6$ and $R^7$ are each independently selected from $C_{1-12}$-alkyl, $C_{3-8}$-cycloalkyl, $C_{6-18}$-aryl, $C_{7-19}$-arylalkyl and $C_{7-19}$-alkylaryl, or where
$R^6$ and $R^7$ together with the nitrogen atom to which they are bonded may form a four-, five- or six-membered ring characterized in that in step (A1), α,α-dihaloalkylamines of the formula (II),

in which
$R^1$ is selected from $C_1$-$C_6$-haloalkyl-ethers or $C_1$-$C_6$-haloalkyl-thioethers;
X is independently selected from F, Cl or Br,
$R^{10}$ and $R^{11}$ are each independently selected from $C_{1-6}$-alkyl, $C_{3-8}$-cycloalkyl,
are reacted in the presence of Lewis Acid with compounds of the formula (III),

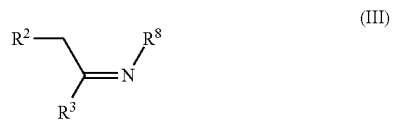

in which
$R^8$ is selected from $C_{1-12}$-alkyl, $C_{3-8}$-cycloalkyl, benzyl;
$R^2$ is selected from H, halogen, COOH, (C=O)O$R^5$, CN and (C=O)N$R^6R^7$;
$R^3$ are each independently selected from $C_1$-$C_6$-haloalkyl alkyl;
$R^5$ is selected from $C_{1-12}$-alkyl, $C_{3-8}$-cycloalkyl, $C_{6-18}$-aryl, $C_{7-19}$-arylalkyl and $C_{7-19}$-alkylaryl;
$R^6$ and $R^7$ are each independently selected from $C_{1-12}$-alkyl, $C_{3-8}$-cycloalkyl, $C_{6-18}$-aryl, $C_{7-19}$-arylalkyl and $C_{7-19}$-alkylaryl, or where
$R^6$ and $R^7$ together with the nitrogen atom to which they are bonded may form a four-, five- or six-membered ring
to form the compound of formula (V-1),

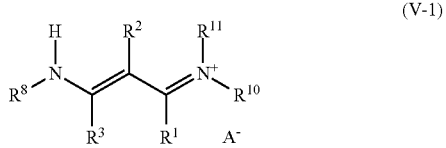

wherein $A^-$ is $BF_4$, $AlCl_3F$, $AlF_2Cl_2$, $AlF_3Cl$;
$R^1$ is selected from $C_1$-$C_6$-haloalkyl-ethers or $C_1$-$C_6$-haloalkyl-thioethers;

$R^2$ is selected from H, halogen, COOH, (C=O)OR$^5$, CN and (C=O)NR$^6$R$^7$;

$R^3$ are each independently selected from $C_1$-$C_6$-haloalkyl alkyl;

$R^5$ is selected from $C_{1-12}$-alkyl, $C_{3-8}$-cycloalkyl, $C_{6-18}$-aryl, $C_{7-19}$-arylalkyl and $C_{7-19}$-alkylaryl;

$R^6$ and $R^7$ are each independently selected from $C_{1-12}$-alkyl, $C_{3-8}$-cycloalkyl, $C_{6-18}$-aryl, $C_{7-19}$-arylalkyl and $C_{7-19}$-alkylaryl, or where $R^6$ and $R^7$ together with the nitrogen atom to which they are bonded may form a four-, five- or six-membered ring $R^8$ is selected from $C_{1-12}$-alkyl, $C_{3-8}$-cycloalkyl, benzyl;

$R^{10}$ and $R^{11}$ are each independently selected from $C_{1-6}$-alkyl, $C_{3-8}$-cycloalkyl, and that in step (B) in the presence of hydrazine

$H_2N$—$NHR^4$ (IV) wherein $R^4$ is selected from H, $C_1$-$C_8$ alkyl, aryl or pyridyl a cyclization of (V-1) takes place to form (Ia/Ib).

In another embodiment of the process according to the invention in a step (A2) compound (V-1) is further reacted with water to compound of formula (V-2)

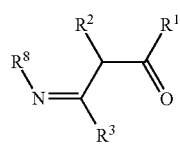

in which $R^1$ is selected from $C_1$-$C_6$-haloalkyl-ethers or $C_1$-$C_6$-haloalkyl-thioethers;

$R^2$ is selected from H, halogen, COOH, (C=O)OR$^5$, CN and (C=O)NR$^6$R$^7$;

$R^3$ are each independently selected from $C_1$-$C_6$-haloalkyl alkyl;

$R^5$ is selected from $C_{1-2}$-alkyl, $C_{3-8}$-cycloalkyl, $C_{6-18}$-aryl, $C_{7-19}$-arylalkyl and $C_{7-19}$-alkylaryl;

$R^6$ and $R^7$ are each independently selected from $C_{1-12}$-alkyl, $C_{3-8}$-cycloalkyl, $C_{6-18}$-aryl, $C_{7-19}$-arylalkyl and $C_{7-19}$-alkylaryl, or where $R^6$ and $R^7$ together with the nitrogen atom to which they are bonded may form a four-, five- or six-membered ring $R^8$ is selected from $C_{1-12}$-alkyl, $C_{3-8}$-cycloalkyl, benzyl;

and that in step (B) in the presence of hydrazine

$H_2N$—$NHR^4$ (IV) wherein $R^4$ is selected from H, $C_1$-$C_8$ alkyl, aryl or pyridyl a cyclization of (V-2) takes place to form (Ia/Ib).

Preferred is a process according to the invention, where the radicals in formula (Ia), (Ib), (II), (III), (IV), (V-1) and (V-2) are defined as follows:

$R^1$ is selected from CHF—OCF$_3$ (fluoro(trifluoromethoxy)methyl), CHF—OC$_2$F$_5$ (fluoro(pentafluoroethoxy)methyl), CHF—SCF$_3$ (fluoro(trifluorothiomethyl)methyl), CHF—SC$_2$F$_5$ fluoro(pentafluorothioethyl)methyl;

$R^2$ is selected from H, F, Cl, Br, COOCH$_3$, COOC$_2$H$_5$, COOC$_3$H$_7$, CN and CON(CH$_3$)$_2$, CON(C$_2$H$_5$)$_2$;

$R^3$ is selected from difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2,2-difluoroethyl, 2,2-dichloro-2-fluoroethyl, 2,2,2-trichloroethyl, tetrafluoroethyl (CF$_3$CFH), pentafluoroethyl and 1,1,1-trifluoroprop-2-yl;

$R^4$ is selected from H, $C_1$-$C_8$ alkyl, aryl, pyridyl;

$R^8$ are each independently selected from methyl, ethyl, n-, iso-propyl, n-, iso-, sec-und t-butyl, cyclopropyl, cyclobutyl, cyclopentyl, cyclohexyl, phenyl, benzyl, phenylethyl, $C_{7-19}$-alkylaryl, tolyl, 2,3-, 2,4-, 2,5-, 2,6-, 3,4- or 3,5-dimethylphenyl;

X is independently selected from F or Cl;

$R^{10}$ and $R^{11}$ are each independently selected from $C_{1-12}$-alkyl, $C_{3-8}$-cycloalkyl, $C_{7-19}$-arylalkyl or $R^{10}$ and $R^{11}$ together with the nitrogen atom to which they are bonded may form a five-membered ring.

More preferred is a process according to the invention, where the radicals in formula (Ia), (Ib), (II), (III), (IV), (V-1) and (V-2) are defined as follows:

$R^1$ is selected from fluoro(trifluoromethoxy)methyl, fluoro(pentafluoroethoxy)methyl;

$R^2$ is selected from H, Cl, CN, COOC$_2$H$_5$;

$R^3$ is selected from trifluoromethyl, difluoromethyl, difluorochloromethyl, pentafluoroethyl;

$R^4$ is selected from H, methyl, ethyl, n-, isopropyl, n-, iso-, sec- and t-butyl, n-pentyl, n-hexyl, 1,3-dimethylbutyl, 3,3-dimethylbutyl, aryl;

$R^8$ is selected from methyl, ethyl, n-, iso-propyl, n-, iso-, sec-und t-butyl, cyclopropyl, cyclobutyl, cyclopentyl, cyclohexyl, benzyl, $C_{7-19}$-alkylaryl;

X is independently selected from F or Cl;

$R^{10}$ and $R^{11}$ are each independently selected from $C_{1-12}$-alkyl, $C_{3-8}$-cycloalkyl.

Even more preferred is a process according to the invention, where the radicals in formula (Ia), (Ib), (II), (III), (IV), (V-1) and (V-2) are defined as follows:

$R^1$ is CHFOCF$_3$, CHFOC$_2$F$_5$;

$R^2$ is selected from H or COOC$_2$H$_5$;

$R^3$ are CF$_2$H, CF$_3$;

$R^4$ is selected form H, methyl, ethyl, phenyl;

$R^8$ is selected from ethyl, n-, iso-propyl, n-, cyclopentyl, cyclohexyl, benzyl;

X is F;

$R^{10}$ and $R^{11}$ are each independently selected from $C_{1-12}$-alkyl.

Most preferred is a process according to the invention, where the radicals in formula (Ia), (Ib), (II), (III), (IV), (V-1) and (V-2) are defined as follows:

$R^1$ is CHFOCF$_3$;

$R^2$ is H;

$R^3$ are CF$_2$H, CF$_3$;

$R^4$ is selected from H, methyl;

$R^8$ is benzyl;

X is F;

$R^{10}$ and $R^{11}$ are each independently selected from methyl, ethyl.

The pyrazoles of the formula (I) can be prepared under the inventive conditions with good yields and in high purity, which means that the process according to the invention overcomes the abovementioned disadvantages of the preparation processes previously described in the prior art.

A further aspect of the present invention are compounds of formula (III-a):

in which
$R^2$ is H,
$R^{3a}$ is $HCF_2$, $CF_3$;
$R^8$ is benzyl.

A further aspect of the present invention are compounds of formula (V-1):

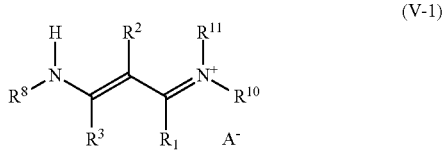

(V-1)

in which the radicals are as defined above
and
$A^-$ is selected from $BF_4$, $AlCl_3F$, $AlF_2Cl_2$, $AlF_3Cl$.

Preferred are compounds of formula (V-1) in which
$R^1$ is selected from $CHFOCF_3$;
$R^2$ is H;
$R^3$ is selected from $CF_2H$, $CF_3$;
$R^8$ is selected from $C_{1-12}$-alkyl, $C_{3-8}$-cycloalkyl and benzyl;
$R^{10}$ and $R^{11}$ are each independently selected from $C_{1-5}$ alkyl;
$A^-$ is selected from $BF_4$, $AlCl_3F$, $AlF_2Cl_2$, $AlF_3Cl$.

A further aspect of the present invention are compounds of formula (V-2):

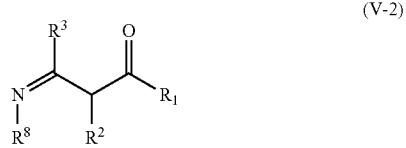

(V-2)

in which the radicals are as defined above.

Preferred are compounds of formula (V-2) in which
$R^1$ is selected from $CHFOCF_3$;
$R^2$ is H;
$R^3$ is selected from $CF_2H$, $CF_3$;
$R^8$ is selected from $C_{1-12}$-alkyl, $C_{3-8}$-cycloalkyl and benzyl.

A further aspect of the present invention are compounds of formula (II-1):

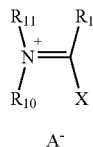

in which
$R^1$ is selected from $C_1$-$C_6$-haloalkyl-ethers or $C_1$-$C_6$-haloalkyl-thioethers;
X is independently selected from F, Cl or Br,
$R^{10}$ and $R^{11}$ are each independently selected from $C_{1-6}$-alkyl, $C_{3-8}$-cycloalkyl and
$A^-$ is selected from $BF_4$, $AlCl_3F$, $AlF_2Cl_2$, $AlF_3Cl$.

General Definitions

In the context of the present invention, the term "halogen" (Hal), unless defined differently, comprises those elements which are selected from the group comprising fluorine, chlorine, bromine and iodine, preferably fluorine, chlorine and bromine, more preferably fluorine and chlorine.

Optionally substituted groups may be mono- or polysubstituted, where the substituents in the case of polysubstitutions may be the same or different.

Haloalkyl: straight-chain or branched alkyl groups having 1 to 6 and preferably 1 to 3 carbon atoms (as specified above), where some or all of the hydrogen atoms in these groups may be replaced by halogen atoms as specified above, for example (but not limited to) $C_1$-$C_3$-haloalkyl such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro, 2-difluoroethyl, 2,2-dichloro-2-fluoroethyl, 2,2,2-trichloroethyl, pentafluoroethyl and 1,1,1-trifluoroprop-2-yl. This definition also applies to haloalkyl as part of a composite substituent, for example haloalkylaminoalkyl etc., unless defined elsewhere. Preference is given to alkyl groups substituted by one or more halogen atoms, for example trifluoromethyl ($CF_3$), difluoromethyl ($CHF_2$), $CF_3CH_2$, $CF_2Cl$ or $CF_3CCl_2$.

Alkyl groups in the context of the present invention, unless defined differently, are linear or branched saturated hydrocarbyl groups. The definition $C_1$-$C_{12}$-alkyl encompasses the widest range defined herein for an alkyl group. Specifically, this definition encompasses, for example, the meanings of methyl, ethyl, n-, isopropyl, n-, iso-, sec- and t-butyl, n-pentyl, n-hexyl, 1,3-dimethylbutyl, 3,3-dimethylbutyl, n-heptyl, n-nonyl, n-decyl, n-undecyl or n-dodecyl.

Alkenyl groups in the context of the present invention, unless defined differently, are linear or branched hydrocarbyl groups containing at least one single unsaturation (double bond). The definition $C_2$-$C_{12}$-alkenyl encompasses the widest range defined herein for an alkenyl group. Specifically, this definition encompasses, for example, the meanings of vinyl; allyl (2-propenyl), isopropenyl (1-methylethenyl); but-1-enyl (crotyl), but-2-enyl, but-3-enyl; hex-1-enyl, hex-2-enyl, hex-3-enyl, hex-4-enyl, hex-5-enyl; hept-1-enyl, hept-2-enyl, hept-3-enyl, hept-4-enyl, hept-5-enyl, hept-6-enyl; oct-1-enyl, oct-2-enyl, oct-3-enyl, oct-4-enyl, oct-5-enyl, oct-6-enyl, oct-7-enyl; non-1-enyl, non-2-enyl, non-3-enyl, non-4-enyl, non-5-enyl, non-6-enyl, non-7-enyl, non-8-enyl; dec-1-enyl, dec-2-enyl, dec-3-enyl, dec-4-enyl, dec-5-enyl, dec-6-enyl, dec-7-enyl, dec-8-enyl, dec-9-enyl; undec-1-enyl, undec-2-enyl, undec-3-enyl, undec-4-enyl, undec-5-enyl, undec-6-enyl, undec-7-enyl, undec-8-enyl, undec-9-enyl, undec-10-enyl; dodec-1-enyl, dodec-2-enyl, dodec-3-enyl, dodec-4-enyl, dodec-5-enyl, dodec-6-enyl, dodec-7-enyl, dodec-8-enyl, dodec-9-enyl, dodec-10-enyl, dodec-11-enyl; buta-1,3-dienyl or penta-1,3-dienyl.

Alkynyl groups in the context of the present invention, unless defined differently, are linear, branched or cyclic hydrocarbyl groups containing at least one double unsaturation (triple bond). The definition $C_2$-$C_{12}$-alkynyl encompasses the widest range defined herein for an alkynyl group. Specifically, this definition encompasses, for example, the meanings of ethynyl (acetylenyl); prop-1-ynyl and prop-2-ynyl.

Cycloalkyl: monocyclic, saturated hydrocarbyl groups having 3 to 8 and preferably 3 to 6 carbon ring members, for example (but not limited to) cyclopropyl, cyclopentyl and cyclohexyl. This definition also applies to cycloalkyl as part of a composite substituent, for example cycloalkylalkyl etc., unless defined elsewhere.

Aryl groups in the context of the present invention, unless defined differently, are aromatic hydrocarbyl groups which may have one, two or more heteroatoms selected from O, N, P and S. The definition $C_{6-18}$-aryl encompasses the widest range defined herein for an aryl group having 5 to 18 skeleton atoms, where the carbon atoms may be exchanged for heteroatoms. Specifically, this definition encompasses, for example, the meanings of phenyl, cycloheptatrienyl, cyclooctatetraenyl, naphthyl and anthracenyl; 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl and 1,3,4-triazol-2-yl; 1-pyrrolyl, 1-pyrazolyl, 1,2,4-triazol-1-yl, 1-imidazolyl, 1,2,3-triazol-1-yl, 1,3,4-triazol-1-yl; 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl.

Arylalkyl groups (aralkyl groups) in the context of the present invention, unless defined differently, are alkyl groups which are substituted by aryl groups, may have one $C_{1-8}$-alkylene chain and may have, in the aryl skeleton, one or more heteroatoms selected from O, N, P and S. The definition $C_{7-19}$-aralkyl group encompasses the widest range defined herein for an arylalkyl group having a total of 7 to 19 atoms in the skeleton and alkylene chain. Specifically, this definition encompasses, for example, the meanings of benzyl and phenylethyl.

Alkylaryl groups (alkaryl groups) in the context of the present invention, unless defined differently, are aryl groups which are substituted by alkyl groups, may have one $C_{1-8}$-alkylene chain and may have, in the aryl skeleton, one or more heteroatoms selected from O, N, P and S. The definition $C_{7-19}$-alkylaryl group encompasses the widest range defined herein for an alkylaryl group having a total of 7 to 19 atoms in the skeleton and alkylene chain. Specifically, this definition encompasses, for example, the meanings of tolyl or 2,3-, 2,4-, 2,5-, 2,6-, 3,4- or 3,5-dimethylphenyl.

The term intermediate used in the context of the present invention describes the substances which occur in the process according to the invention and are prepared for further chemical processing and are consumed or used therein in order to be converted to another substance. The intermediates can often be isolated and intermediately stored or are used without prior isolation in the subsequent reaction step. The term "intermediate" also encompasses the generally unstable and short-lived intermediates which occur transiently in multistage reactions (staged reactions) and to which local minima in the energy profile of the reaction can be assigned.

The inventive compounds may be present as mixtures of any different isomeric forms possible, especially of stereoisomers, for example E and Z isomers, threo and erythro isomers, and optical isomers, but if appropriate also of tautomers. Both the E and the Z isomers are disclosed and claimed, as are the threo and erythro isomers, and also the optical isomers, any mixtures of these isomers, and also the possible tautomeric forms.

Process Description

The process is illustrated in Scheme 1:

Scheme 1:

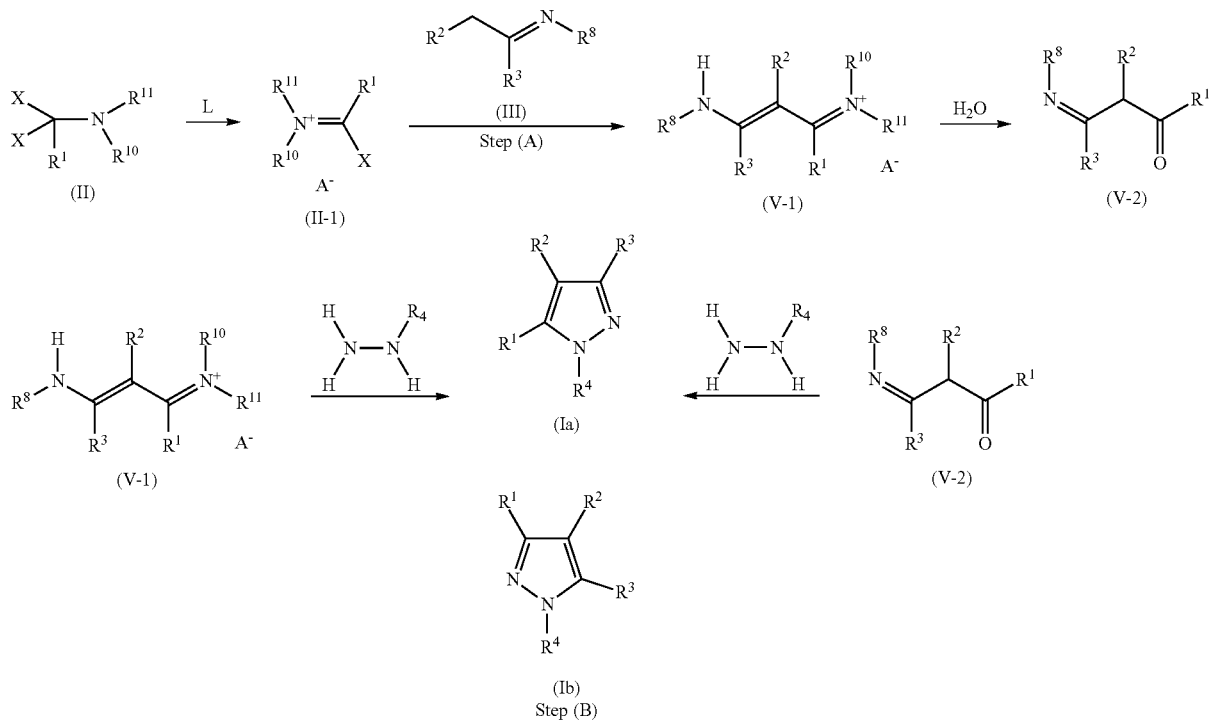

Step (A)

In step (A), α,α-dihaloalkylamines of the formula (II) are first reacted, in the presence of a Lewis acid [L], with compounds of the formula (III) to form compounds of formula (II-1). Compounds of formula (II-1) are new.

Preferred compounds of the general formula (II) are N,N-dimethyl-1,1,2-trifluoro-2-(trifluoromethoxy)-ethanamine, N,N-diethyl-1,1,2-trifluoro-2-(trifluoromethoxy)-ethanamine, N,N-dimethyl-1,1,2-trifluoro-2-(pentafluoroethoxy)-ethanamine, N,N-diethyl-1,1,2-trifluoro-2-(pentafluoroethoxy)-ethanamine, N,N-dimethyl-1,1,2-trifluoro-2-(trifluorothiomethyl)-ethanamine, and N,N-diethyl-1,1,2-trifluoro-2-(trifluorothiomethyl)-ethanamine.

Compounds of the general formula (II) are used as aminoalkylating agents. Preference is given to N,N-dimethyl-1,1,2-trifluoro-2-(trifluoromethoxy)-ethanamine, N,N-diethyl-1,1,2-trifluoro-2-(trifluoromethoxy)-ethanamine. These α,α-dihaloamines can be prepared (cf. Maslennikov, I. G.; Eremin, K. I. Russ. J. Gen. Chem. 2011, 81, 1741-1742, CAN 155:509447).

In a preferred embodiment of the process according to the invention, the α,α-dihaloalkylamine is first reacted with Lewis acid [L], for example $BF_3$, $AlCl_3$, $AlF_2Cl_2$, $AlF_3Cl$ and then the mixture of the compound of the formula (III) is added in substance or dissolved in a suitable solvent (cf. WO 2008/022777).

α,α-Dihaloalkylamines are reacted with Lewis acids (preparation of the iminium salts of the formula (II-1) according to the teaching of WO 2008/022777. According to the invention, the reaction is effected at temperatures of −20° C. to +40° C., preferably at temperatures of −20° C. to +30° C., more preferably at −10 to 20° C. and under standard pressure. Due to the hydrolysis sensitivity of the α,α-dihaloalkylamines, the reaction is conducted in anhydrous apparatus under inert gas atmosphere.

The reaction time is not critical and may, according to the batch size and temperature, be selected within a range between a few minutes and several hours.

According to the invention, 1 mol of the Lewis acid [L] is reacted with equimolar amounts of the α,α-dihaloalkylamine of the formula (II).

For the process according to the invention 1 to 2 mol, preferred 1 to 1.5 mol, most preferred 1 to 1.2 mol of the α,α-dihaloalkylamine of the formula (II) is reacted with 1 mol compound of formula (III).

Suitable solvents are, for example, aliphatic, alicyclic or aromatic hydrocarbons, for example petroleum ether, n-hexane, n-heptane, cyclohexane, methylcyclohexane, benzene, toluene, xylene or decalin, and halogenated hydrocarbons, for example chlorobenzene, dichlorobenzene, dichloromethane, chloroform, tetrachloromethane, dichloroethane or trichloroethane, ethers such as diethyl ether, diisopropyl ether, methyl tert-butyl ether, methyl tert-amyl ether, dioxane, tetrahydrofuran, 1,2-dimethoxyethane, 1,2-diethoxyethane or anisole; nitriles such as acetonitrile, propionitrile, n- or isobutyronitrile or benzonitrile; amides such as N,N-dimethylformamide, N,N-dimethylacetamide, N-methylformanilide, N-methylpyrrolidone or hexamethylphosphoramide; sulphoxides such as dimethyl sulphoxide or sulphones such as sulpholane. Particular preference is given, for example, to THF, acetonitriles, ethers, toluene, xylene, chlorobenzene, n-hexane, cyclohexane or methylcyclohexane, and very particular preference, for example, to acetonitrile, THF, ether or dichloromethane.

The intermediates of the formula (V-1) can be used in the cyclization step without prior workup.

Alternatively, the intermediates (V-1) can be isolated by suitable workup steps, characterized and optionally further purified or transformed into enaminoketones (V-2).

Compounds (V-2) are formed during the treatment of compounds (V-1) with water. In order to achieve the full transformation of (V-1) into (V-2), 1 mol to 50 mol, preferably 2 to 20 mol of the water for 1 mol of the compound of formula (V-1) is used. This transformation proceeds without solvent exchange. Compounds (V-2) could also be isolated and additionally purified, or directly converted in step (B) to the pyrazole of Formula (I) upon their treatment with hydrazine of the formula $NH_2$—$NHR^4$.

Starting ketimines (III) can be prepared from ketones (VII) and amines (VI).

Scheme 2:

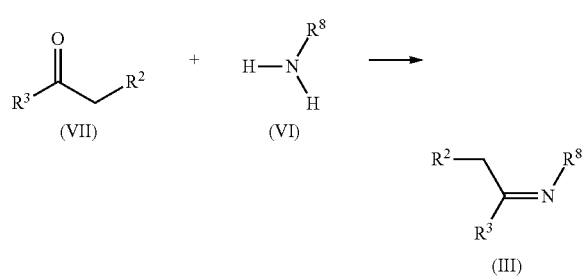

The reaction of compound (VII) and (VI) according to the invention is effected at temperatures of −40° C. to +120° C., preferably at temperatures of +20° C. to +100° C., more preferably at 20° C. to +60° C. and under standard pressure.

For the process according to the invention 0.9 to 2 mol, preferred 1 to 1.8 mol, most preferred 1 to 1.5 mol of the compound of the formula (VI) is reacted with 1 mol compound of the formula (VII).

The reaction time is not critical and may, according to the batch size and temperature, be selected within a range between a few and many hours.

Suitable solvents are, for example, aliphatic, alicyclic or aromatic hydrocarbons, for example petroleum ether, n-hexane, n-heptane, cyclohexane, methylcyclohexane, benzene, toluene, xylene or decalin, and halogenated hydrocarbons, for example chlorobenzene, dichlorobenzene, dichloromethane, chloroform, tetrachloromethane, dichloroethane or trichloroethane, ethers such as diethyl ether, diisopropyl ether, methyl tert-butyl ether, methyl tert-amyl ether, dioxane, tetrahydrofuran, 1,2-dimethoxyethane, 1,2-diethoxyethane or anisole; nitriles such as acetonitrile, propionitrile, n- or isobutyronitrile or benzonitrile; amides such as N,N-dimethylformamide, N,N-dimethylacetamide, N-methylformanilide, N-methylpyrrolidone or hexamethylphosphoramide; sulphoxides such as dimethyl sulphoxide or sulphones such as sulpholane, alkohols such as methanol, ethanol, isopropanolm butanol. Particular preference is given, for example, to THF, acetonitriles, ethers, toluene, xylene, chlorobenzene, n-hexane, cyclohexane or methylcyclohexane, ethanol and very particular preference, for example, to acetonitrile, THF, ether, dichloromethane, ethanol.

Step (B)

According to the invention, 1 mol to 2 mol, preferably 1 to 1.5 mol of the hydrazine of the formula $NH_2$—NHR for 1 mol of the compound of formula (V-1 or V-2) is used.

The cyclization in step (B) of the compound of formula (V-1 or V-2) is effected at temperatures of −40° C. to +80° C., preferably at temperatures of +20° C. to +70° C., more preferably at 30° C. to +60° C. and under standard pressure.

The reaction time is not critical and may, according to the batch size, be selected within a relatively wide range.

Typically, the cyclization step (B) is effected without changing the solvent.

Typically the cyclization of compound of the formula (V-1 and V-2) proceeds under acidic condition.

Preference is given to mineral acids, for example $H_2SO_4$, HCl, HF, HBr, HI, $H_3PO_4$ or organic acids, for example CH3COOH, $CF_3COOH$, p-toluenesulphonic acid, methanesulphonic acid, trifluoromethanesulphonic acid.

According to the invention, 0.1 mol to 2 mol, preferably 0.1 to 1.5 mol of the acid for 1 mol of the compound of formula (V-I, V-II) is used. Suitable solvents are, for example, aliphatic, alicyclic or aromatic hydrocarbons, for example petroleum ether, n-hexane, n-heptane, cyclohexane, methylcyclohexane, benzene, toluene, xylene or decalin, and halogenated hydrocarbons, for example chlorobenzene, dichlorobenzene, dichloromethane, chloroform, tetrachloromethane, dichloroethane or trichloroethane, ethers such as diethyl ether, diisopropyl ether, methyl tert-butyl ether, methyl tert-amyl ether, dioxane, tetrahydrofuran, 1,2-dimethoxyethane, 1,2-diethoxyethane or anisole; alcohols such as methanol, ethanol, isopropanol or butanol, nitriles such as acetonitrile, propionitrile, n- or isobutyronitrile or benzonitrile; amides such as N,N-dimethylformamide, N,N-dimethylacetamide, N-methylformanilide, N-methylpyrrolidone or hexamethylphosphoramide; sulphoxides such as dimethyl sulphoxide or sulphones such as sulpholane. Particular preference is given, for example, to acetonitrilestoluene, xylene, chlorobenzene, n-hexane, cyclohexane or methylcyclohexane, and very particular preference, for example, to acetonitriles, THF, toluene or xylene. After the reaction has ended, for example, the solvents are removed and the product is isolated by filtration, or the product is first washed with water and extracted, the organic phase is removed and the solvent is removed under reduced pressure.

The compounds of the formula (Iab) where $R^2=COOR^4$ can then be converted to pyrazole acids of the formula (I) $R^2=COOH$.

The inventive compounds (Ia) and (Ib) are used for preparation of active fungicidal ingredients.

EXAMPLE 1

N,N-dimethyl-1,1,2-trifluoro-2-(trifluoromethoxy)-ethanamine (II-1)

1,1,2-trifluoro-2-(trifluoromethoxy)ethene (0.44 mL, 3.97 mmol) was liquefied at −78° C. into a sealed tube equipped with a magnetic stirbar under inert atmosphere using a dry ice/acetone bath. A solution of dimethylamine (2M in THF, 2 mL, 4 mmol) was added via syringe, the mixture was raised to max. 20° C. over 20 min to avoid polymerization of THF. The formed product was used for further transformation without purification.

EXAMPLE 2

3-(fluoro(trifluoromethoxy)methyl)-5-(trifluoromethyl)-1H-pyrazole (I-1)

To the mixture solution of the N,N-dimethyl-1,1,2-trifluoro-2-(trifluoromethoxy)-ethanamine (II-1) (3.95 mmol) was added $BF_3$-$Et_2O$ (0.5 mL, 3.95 mmol) via syringe. The solution was vigorously stirred for 15 min. The resulting biphasic mixture was then added onto a solution of N-benzyl-1,1,1-trifluoropropan-2-imine (660 mg, 3.28 mmol) in distilled THF (4 mL) under inert atmosphere into a Schlenk vessel via syringe. The mixture was stirred at room temperature for 30 min. Hydrazine hydrate (0.24 mL, 4.89 mmol) was added via syringe, rapidly followed by conc. $H_2SO_4$ (0.08 mL, 1.5 mmol), both via syringe. The mixture was further stirred 1 h at room temperature. The mixture was then evaporated in vacuo (>200 mbar, 45° C. max).

The crude product was purified by flash chromatography ($Et_2O$ in pentane 0 to 20%).

Yield: 500 mg, 60%; brown oil.

$^1$H NMR (400 MHz, CDCl$_3$; Me$_4$Si): δ=12.2 (s. br, NH), 6.78 (d, CHFOCF$_3$, $^2J_{H-F}$=57.5 Hz), 6.77 (s, CH$_{arom}$), ppm.

$^{19}$F NMR (376 MHz, CDCl$_3$; CFCl$_3$): δ=−60.0 (d, CHFOCF$_3$, $^4J_{H-F}$=5 Hz), −62.3 (s, CF$_3$), −121.7 (qd, CHFOCF$_3$, $^2J_{H-F}$=57 Hz, $^4J_{H-F}$=5 Hz) ppm.

$^{13}$C NMR (100 MHz, CDCl$_3$; Me$_4$Si): δ=140.8 (m, CCF$_3$ and CCHFOCF$_3$), 120.3 and 121.0 (CF$_3$ and OCF$_3$, $^1J_{C-F}$=269 and 262 Hz), 104.0 (CH$_{arom}$), 99.1 (dd, CHFOCF$_3$, $^1J_{C-F}$=230 Hz, $^3J_{C-F}$=3.5 Hz) ppm.

HRMS (ESI) calcd for C$_6$H$_4$F$_7$N$_2$O [M+H]: 253.0206. Found: 253.0213.

EXAMPLE 3

3-(fluoro(trifluoromethoxy)methyl)-5-(perfluoroethyl)-1H-pyrazole (I-2)

(preparation see Example 2 using N-benzyl-3,3,4,4,4-pentafluorobutan-2-imine (500 mg, 1.73 mmol) and II-1 (2.08 mmol)).

Yield: 99% (by $^{19}$F NMR); yellow oil.

$^1$H NMR (400 MHz, CDCl$_3$; Me$_4$Si): δ=12.59 (s. br, NH), 6.82 (s, CH$_{arom}$), 6.79 (d, CHFOCF$_3$, $^2J_{H-F}$=57.5 Hz) ppm.

$^{19}$F NMR (376 MHz, CDCl$_3$; CFCl$_3$): δ=−59.9 (d, CHFOCF$_3$, $^4J_{H-F}$=5 Hz), −85.1 (s, CF$_2$CF$_3$), −113.6 (s, CF$_2$CF$_3$), −121.8 (dq, CHFOCF$_3$, $^2J_{H-F}$=57.4 Hz, $^4J_{H-F}$=4.9 Hz) ppm.

$^{13}$C NMR (100 MHz, CDCl$_3$; Me$_4$Si): δ=140.9 and 139.2 (m, CCHFOCF$_3$ and CC$_2$F$_5$), 120.7 (q, CHFOCF$_3$, J=263 Hz), 118.4 (qt, CF$_2$CF$_3$, $^1J_{C-F}$=286 Hz, $^2J_{C-F}$=40 Hz), 109.8 (tq, CF$_2$CF$_3$, $^1J_{C-F}$=252 Hz, $^2J_{C-F}$=40 Hz), 105.2 (CH$_{arom}$), 98.8 (dd, CHFOCF$_3$, $^1J_{C-F}$=230 Hz, $^3J_{C-F}$=2.5 Hz) ppm.

HRMS (ESI) calcd for C$_7$H$_4$F$_9$N$_2$O [M+H]: 303.0174. Found: 303.0168. b.p. 80-82° C.

EXAMPLE 4

Mixture 3-(difluoromethyl)-5-(fluoro(trifluoromethoxy)methyl)-1-methyl-1H-pyrazole and 5-(difluoromethyl)-3-(fluoro(trifluoromethoxy)methyl)-1-methyl-1H-pyrazole (7:3)

(preparation see Example 2, using N-benzyl-1,1-difluoropropan-2-imine (3.35 mmol) and II-1 (3.97 mmol))

Yield: 84% (by $^{19}$F NMR, 7/3 I-3:I-4, both isomers separated by chromatography); both yellow oils.

3-(difluoromethyl)-5-(fluoro(trifluoromethoxy)methyl)-1-methyl-1H-pyrazole (I-3)

$^1$H NMR (400 MHz, CDCl$_3$; Me$_4$Si): δ=6.71 (dt, CHF$_2$, $^2J_{H-F}$=53.5 Hz, $^4J_{H-F}$=1.2 Hz), 6.70 (d, CHFOCF$_3$, $^2J_{H-F}$=57 Hz), 4.00 (s, NCH$_3$), 6.68 (s, CH$_{arom}$) ppm.

$^{19}$F NMR (376 MHz, CDCl$_3$; CFCl$_3$): δ=−59.3 (m, OCF$_3$), −113.4 (m, CHF$_2$, $^2J_{H-F}$=53.5 Hz), −119.8 (d, CHFOCF$_3$, $^2J_{H-F}$=57.5 Hz) ppm.

$^{13}$C NMR (100 MHz, CDCl$_3$; Me$_4$Si): δ=144.8 (d, CCH-FOCF$_3$, $^2J_{C-F}$=29 Hz), 136.9 (t, CCHF$_2$, $^2J_{C-F}$=26 Hz), 121.1 (q, OCF$_3$, 1$J_{C-F}$=261 Hz), 108.3 (t, CHF$_2$, $^1J_{C-F}$=237 Hz), 105.3 (t, CH$_{arom}$), 101.0 (qd, CHFOCF3, $^1J_{C-F}$=227 Hz, $^3J_{C-F}$=4 Hz), 38.5 (NCH$_3$), ppm.

HRMS (ESI) calcd for C$_7$H$_7$F$_6$N$_2$O [M+H]: 249.0457. Found: 249.0460.

5-(difluoromethyl)-3-(fluoro(trifluoromethoxy)methyl)-1-methyl-1H-pyrazole (I-4)

$^1$H NMR (400 MHz, CDCl$_3$; Me$_4$Si): δ=6.76 (d, CHFOCF$_3$, $^2J_{H-F}$=56 Hz), 6.68 (s, CH$_{arom}$), 6.64 (t, CHF$_2$, $^2J_{H-F}$=55 Hz), 3.98 (s, NCH$_3$) ppm.

$^{19}$F NMR (376 MHz, CDCl$_3$; CFCl$_3$): δ=−59.6 (d, OCF$_3$, $^4J_{H-F}$=5.5 Hz), −112.2 (d, CHF$_2$, $^2J_{H-F}$=55 Hz), −121.6 (qd, CHFOCF$_3$, $^2J_{H-F}$=56 Hz, $^4J_{H-F}$=5.5 Hz) ppm.

$^{13}$C NMR (100 MHz, CDCl$_3$; Me$_4$Si): δ=145.7 (t, CCHF$_2$, $^2J_{C-F}$=30 Hz), 135.5 (d, CCHFOCF$_3$, $^2J_{C-F}$=26 Hz), 120.8 (q, OCF$_3$, 1$J_{C-F}$=263 Hz), 110.5 (t, CHF$_2$, 1$J_{C-F}$=234 Hz), 104.8 (CH$_{arom}$), 98.5 (qd, CHFOCF$_3$, $^1J_{C-F}$=228 Hz, $^3J_{C-F}$=4 Hz), 38.5 (NCH$_3$), ppm.

HRMS calcd for C$_7$H$_7$F$_6$N$_2$O [M+H]: 249.0457. Found: 249.0458.

EXAMPLE 5

3-(fluoro(trifluoromethoxy)methyl)-1-methyl-5-(trifluoromethyl)-1H-pyrazole (I-5)

(preparation according to example 2, using N-benzyl-1,1,1-trifluoropropan-2-imine (3.35 mmol) and II-1 (3.97 mmol))

Yield: 66% (by $^{19}$F NMR); yellow oil.

$^1$H NMR (400 MHz, CDCl$_3$; Me$_4$Si): δ=6.84 (s, CH$_{arom}$), 6.71 (d, CHFOCF$_3$, $^2J_{H-F}$=57 Hz), 4.02 (s, NCH$_3$) ppm.

$^{19}$F NMR (376 MHz, CDCl$_3$; CFCl$_3$): δ=−59.3 (d, CHFOCF$_3$, $^4J_{H-F}$=5 Hz), −60.9 (s, CF$_3$), −120.1 (qd, CHFOCF$_3$, $^2J_{H-F}$=57 Hz, $^4J_{H-F}$=5.4 Hz) ppm.

$^{13}$C NMR (100 MHz, CDCl$_3$; Me$_4$Si): δ=144.8 (d, CCH-FOCF$_3$, $^1J_{C-F}$=30 Hz), 133.6 (CCF$_3$, $^2J_{C-F}$=40 Hz), 121.0 and 119.6 (q, OCF$_3$ and CF$_3$, $^1J_{C-F}$=261 and 269 Hz), 105.8 (CH$_{arom}$), 100.8 (qd, CHFOCF$_3$, $^1J_{C-F}$=227 Hz, $^3J_{C-F}$=4 Hz), 38.6 (NCH$_3$) ppm.

HRMS (ESI) calcd for C$_7$H$_6$F$_7$N$_2$O [M+H]: 267.0363. Found: 267.0347.

EXAMPLE 6

3-(fluoro(trifluoromethoxy)methyl)-1-methyl-5-(perfluoroethyl)-1H-pyrazole (I-6)

(preparation according to example 2, using N-benzyl-1,1,1-trifluoropropan-2-imine (3.35 mmol) and II-1 (3.97 mmol))

Yield: 81% (by $^{19}$F NMR); yellow oil.

$^1$H NMR (400 MHz, CDCl$_3$; Me$_4$Si): δ=6.84 (s, CH$_{arom}$), 6.72 (d, CHFOCF$_3$, $^2J_{H-F}$=57.2 Hz), 4.04 (s, NCH$_3$) ppm.

$^{19}$F NMR (376 MHz, CDCl$_3$; CFCl$_3$): δ=−59.3 (d, CHFOCF$_3$, $^2J_{H-F}$=5.4 Hz), −83.9 (s, CF$_2$CF$_3$), −110.7 (CF$_2$CF$_3$), −120.3 (dq, CHFOCF$_3$, $^2J_{H-F}$=57.2 Hz, $^4J_{H-F}$=5.3 Hz) ppm.

$^{13}$C NMR (100 MHz, CDCl$_3$; Me$_4$Si): δ=145.2 (d, CCH-FOCF$_3$, $^2J_{C-F}$=29.5 Hz), 131.6 (t, CC$_2$F$_5$, $^2J_{C-F}$=28.7 Hz), 121.1 (q, CHFOCF$_3$, $^1J_{C-F}$=262 Hz), 118.6 (qt, CF$_2$CF$_3$, $^1J_{C-F}$=286.3 Hz, $^2J_{C-F}$=37.2 Hz), 109.9 (tq, CF$_2$CF$_3$, $^1J_{C-F}$=253.5 Hz, $^2J_{C-F}$=40 Hz), 107.4 (CH$_{arom}$), 100.7 (dd, CHFOCF$_3$, $^1J_{C-F}$=227.4 Hz, $^4J_{C-F}$=4.3 Hz), 39.5 (NCH$_3$) ppm.

HRMS (ESI) calcd for C$_8$H$_6$F$_9$N$_2$O [M+H]: 317.0331. Found: 317.0298.

EXAMPLE 7

(E/Z)—N-(4-(benzylamino)-1,5,5-trifluoro-1-(trifluoromethoxy)pent-3-en-2-ylidene)-N-methylmethanaminium tetrafluoroborate (V-1-1)

1,1,2-trifluoro-2-(trifluoromethoxy)ethene (0.44 mL, 3.97 mmol) was liquefied at −78° C. into a sealed tube equipped with a magnetic stirbar under inert atmosphere using a dry ice/acetone bath. A solution of dimethylamine (2M in THF, 2 mL, 4 mmol) was added via syringe, the mixture was raised to max. 20° C. over 20 min. BF$_3$-Et$_2$O (0.51 mL, 4.02 mmol) was added via syringe, the solution was vigorously stirred for 15 min. The resulting biphasic mixture was then added onto a solution of N-benzyl-1,1-difluoropropan-2-imine (728 mg, 3.97 mmol) in distilled THF (0.8-1 mol/L) under inert atmosphere into a Schlenk vessel via syringe. The mixture was stirred at room temperature for 30 min. The mixture was directly concentrated in vacuo, to yield the vinamidinium intermediate as thick orange oil (1.62 g, 92%).

$^1$H NMR (400 MHz, CD$_3$CN; Me$_4$Si): δ=8.33 (s. br, NH), 7.47 to 7.35 (m, 5H, arom), 6.81 (d, CHFOCF$_3$, $^2J_{H-F}$=54.1 Hz), 6.64 (t, CHF$_2$, $^2J_{H-F}$=52.6 Hz), 5.14 (s, CHCN(Me)$_2$), 4.56 (d, CH$_2$NH), 3.35 (s. br, C=N(CH$_3$)$_2$) ppm.

$^{19}$F NMR (376 MHz, CD$_3$CN; CFCl$_3$): δ=−59.8 (d, CHFOCF$_3$, $^4J_{H-F}$=4.8 Hz), −120.6 (d, CHF$_2$, $^2J_{H-F}$=53.1 Hz), −129.1 (d, CHFOCF$_3$, $^2J_{H-F}$=54.5 Hz), −151.5 (s, BF$_4^-$) ppm.

$^{13}$C NMR (100 MHz, CD$_3$CN; Me$_4$Si): δ=164.6 (d, COCHFOCF$_3$, $^2J_{C-F}$=25.4 Hz), 159.9 (t, CCHF$_2$, $^2J_{C-F}$=23.3 Hz), 135.4, 130.0, 129.5, 129.0 (arom.), 121.6 (q, OCF$_3$, 1$J_{C-F}$=263.3 Hz), 111.0 (td, CHF$_2$, $^1J_{C-F}$=244.8 Hz, $^5J_{C-F}$=4.3 Hz), 100.9 (d, CHFOCF$_3$, 1$J_{C-F}$=238.3 Hz), 87.3 (CHCN$^+$(Me)$_2$), 49.8 (CH$_2$NH) ppm.

EXAMPLE 8

(E/Z)-4-(benzylamino)-1,5,5-trifluoro-1-(trifluoromethoxy)pent-3-en-2-one (V-2-1)

(E/Z)—N-(4-(b enzylamino)-1,5,5-trifluoro-1-(trifluoromethoxy)pent-3-en-2-ylidene)-N-methylmethanaminium tetrafluoroborate (V-1-1) (1.62 g, 3.66 mmol) was dissolved in 10 ml of Et$_2$O before 1 ml of water and 1 mL of 1N HCl were added followed by a vigorous stirring of the mixture (pH of the solution between 3-4). The mixture was stirred for 1 h at RT, and the organic layer was separated, dried over Na$_2$SO$_4$, filtered and evaporated in vacuo, to yield (V-2-1) as orange oil (1.08 g, 3.30 mmol, 83%).

$^1$H NMR (400 MHz, CDCl$_3$; Me$_4$Si): δ=10.64 (s. br, NH), 7.40 to 7.28 (m, 5H, arom), 6.18 (t, CHF$_2$, $^2J_{H-F}$=53.2 Hz), 5.81 (d, CHFOCF$_3$, $^2J_{H-F}$=56.9 Hz), 5.68 (s, CHCO), 4.65 (d, CH$_2$NH) ppm.

$^{19}$F NMR (376 MHz, CDCl$_3$; CFCl$_3$): δ=−59.3 (d, CHFOCF$_3$, $^4J_{H-F}$=4.7 Hz), −119.3 (d, CHF$_2$, $^2J_{H-F}$=53.1 Hz), −135.5 (dq, CHFOCF$_3$, $^2J_{H-F}$=56.6 Hz, $^4J_{H-F}$=4.6 Hz) ppm.

$^{13}$C NMR (100 MHz, CDCl$_3$; Me$_4$Si): δ=185.5 (d, C=O, $^2J_{C-F}$=25.3 Hz), 157.3 (t, CCHF$_2$, $^2J_{C-F}$=22.0 Hz), 136.1, 129.2, 128.4, 127.3 (arom), 121.2 (q, OC- $F_3$, $^1J_{C-F}$=261 Hz), 111.0 (t, $CHF_2$, $^1J_{C-F}$=245 Hz), 101.3 (dq, $CHFOCF_3$, $^1J_{C-F}$=245 Hz, $^3J_{C-F}$=2.5 Hz), 87.8 (t, CHCO, $^3J_{C-F}$=77.2 Hz), 48.1 ($CH_2NH$) ppm.

An interaction of (V-2-1) with hydrazine-hydrate according to the example 2 gave 5-(difluoromethyl)-3-(fluoro (trifluoromethoxy)methyl)-1H-pyrazole in 85% yield.

The invention claimed is:

1. A process for preparing a 3,5-bis(haloalkyl)pyrazole of formula (Ia) or (Ib)

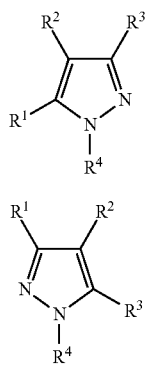

wherein:
$R^1$ is selected from the group consisting of $C_1$-$C_6$-haloalkyl-ether and $C_1$-$C_6$-haloalkyl-thioether;
$R^2$ is selected from the group consisting of H, halogen, COOH, (C=O)$OR^5$, CN and (C=O)$NR^6R^7$;
$R^3$ is $C_1$-$C_6$-haloalkyl;
$R^4$ is selected from the group consisting of H, $C_1$-$C_8$ alkyl, aryl and pyridyl;
$R^5$ is selected from the group consisting of $C_{1-12}$-alkyl, $C_{3-8}$-cycloalkyl, $C_{6-18}$-aryl, $C_{7-19}$-arylalkyl and $C_{7-19}$-alkylaryl; and
$R^6$ and $R^7$ are independently selected from the group consisting of $C_{1-12}$-alkyl, $C_{3-8}$-cycloalkyl, $C_{6-18}$-aryl, $C_{7-19}$-arylalkyl and $C_{7-19}$-alkylaryl,
or
$R^6$ and $R^7$ are taken together with the nitrogen atom to which they are attached to form a four-, five- or six-membered ring,
comprising: step (A1), reacting an α,α-dihaloalkylamine of formula (II)

wherein:
$R^1$ is selected from the group consisting of $C_1$-$C_6$-haloalkyl-ether and $C_1$-$C_6$-haloalkyl-thioether;
each X is independently selected from the group consisting of F, Cl and Br; and
$R^{10}$ and $R^{11}$ are independently selected from the group consisting of $C_{1-6}$-alkyl and $C_{3-8}$-cycloalkyl,
in the presence of a Lewis Acid with a compound of formula (III)

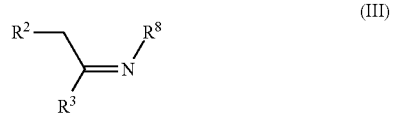

wherein:
$R^8$ is selected from the group consisting of $C_{1-12}$-alkyl, $C_{3-8}$-cycloalkyl and benzyl;
$R^2$ is selected from the group consisting of H, halogen, COOH, (C=O)$OR^5$, CN and (C=O)$NR^6R^7$;
$R^3$ is $C_1$-$C_6$-haloalkyl;
$R^5$ is selected from the group consisting of $C_{1-12}$-alkyl, $C_{3-8}$-cycloalkyl, $C_{6-18}$-aryl, $C_{7-19}$-arylalkyl and $C_{7-19}$-alkylaryl; and
$R^6$ and $R^7$ are independently selected from the group consisting of $C_{1-12}$-alkyl, $C_{3-8}$-cycloalkyl, $C_{6-18}$-aryl, $C_{7-19}$-arylalkyl and $C_{7-19}$-alkylaryl,
or
$R^6$ and $R^7$ are taken together with the nitrogen atom to which they are attached to form a four-, five- or six-membered ring,
to form a compound of formula (V-1)

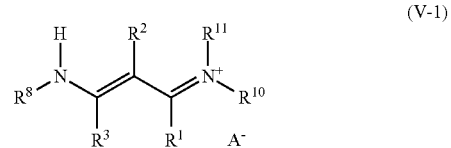

wherein:
$A^-$ is $BF_4$, $AlCl_3F$, $AlF_2Cl_2$ or $AlF_3Cl$;
$R^1$ is selected from the group consisting of $C_1$-$C_6$-haloalkyl-ether and $C_1$-$C_6$-haloalkyl-thioether;
$R^2$ is selected from the group consisting of H, halogen, COOH, (C=O)$OR^5$, CN and (C=O)$NR^6R^7$;
$R^3$ is $C_1$-$C_6$-haloalkyl;
$R^5$ is selected from the group consisting of $C_{1-12}$-alkyl, $C_{3-8}$-cycloalkyl, $C_{6-18}$-aryl, $C_{7-19}$-arylalkyl and $C_{7-19}$-alkylaryl;
$R^6$ and $R^7$ are independently selected from the group consisting of $C_{1-12}$-alkyl, $C_{3-8}$-cycloalkyl, $C_{6-18}$-aryl, $C_{7-19}$-arylalkyl and $C_{7-19}$-alkylaryl,
or
$R^6$ and $R^7$ are taken together with the nitrogen atom to which they are attached to form a four-, five- or six-membered ring;
$R^8$ is selected from the group consisting of $C_{1-12}$-alkyl, $C_{3-8}$-cycloalkyl and benzyl; and
$R^{10}$ and $R^{11}$ are independently selected from the group consisting of $C_{1-6}$-alkyl and $C_{3-8}$-cycloalkyl,
and step (B), cyclizing the compound of formula (V-1) in the presence of a hydrazine of formula (IV)

wherein:
$R^4$ is selected from the group consisting of H, $C_1$-$C_8$ alkyl, aryl and pyridyl, to form the compound of formula (Ia) or (Ib).

2. The process according to claim 1, comprising step (A2), wherein the compound of formula (V-1) is further reacted with water to form a compound of formula (V-2)

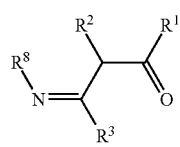

(V-2)

wherein:
R¹ is selected from the group consisting of $C_1$-$C_6$-haloalkyl-ether and $C_1$-$C_6$-haloalkyl-thioether;
R² is selected from the group consisting of H, halogen, COOH, (C=O)OR⁵, CN and (C=O)NR⁶R⁷;
R³ is $C_1$-$C_6$-haloalkyl;
R⁵ is selected from the group consisting of $C_{1-12}$-alkyl, $C_{3-8}$-cycloalkyl, $C_{6-18}$-aryl, $C_{7-19}$-arylalkyl and $C_{7-19}$-alkylaryl;
R⁶ and R⁷ are independently selected from the group consisting of $C_{1-12}$-alkyl, $C_{3-8}$-cycloalkyl, $C_{6-18}$-aryl, $C_{7-19}$-arylalkyl and $C_{7-19}$-alkylaryl,
or
R⁶ and R⁷ are taken together with the nitrogen atom to which they are attached to form a four-, five- or six-membered ring; and
R⁸ is selected from the group consisting of $C_{1-12}$-alkyl, $C_{3-8}$-cycloalkyl and benzyl;
and step (B), wherein the compound of formula (V-2) is cyclized in the presence of the hydrazine of formula (IV)

$$H_2N—NHR^4 \quad (IV)$$

wherein:
R⁴ is selected from the group consisting of H, $C_1$-$C_8$ alkyl, aryl and pyridyl, to form (Ia/Ib) to form the compound of formula (Ia) or (Ib).

3. A process for preparing a 3,5-bis(haloalkyl)pyrazole of formula (Ia) or (Ib)

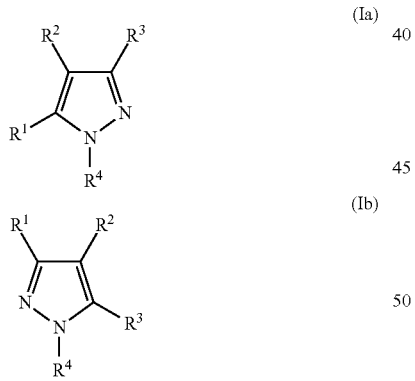

wherein:
R¹ is selected from the group consisting of CHF—OCF₃ (fluoro(trifluoromethoxy)methyl), CHF—OC₂F₅ (fluoro(pentafluoroethoxy)methyl), CHF—SCF₃ (fluoro(trifluorothiomethyl)methyl), and CHF—SC₂F₅ fluoro(pentafluorothioethyl)methyl;
R² is selected from the group consisting of H, F, Cl, Br, COOCH₃, COOC₂H₅, COOC₃H₇, CN, CON(CH₃)₂ and CON(C₂H₅)₂;
R³ is selected from the group consisting of difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-difluoroethyl, 2,2-dichloro-2-fluoroethyl, 2,2,2-trichloroethyl, tetrafluoroethyl (CF₃CFH), pentafluoroethyl, and 1,1,1-trifluoroprop-2-yl; and
R⁴ is selected from the group consisting of H, $C_1$-$C_8$ alkyl, aryl and pyridyl, comprising: step (A1), reacting an α,α-dihaloalkylamine of formula (II)

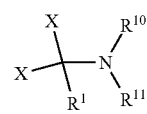

wherein:
R¹ is selected from the group consisting of CHF—OCF₃ (fluoro(trifluoromethoxy)methyl), CHF—OC₂F₅ (fluoro(pentafluoroethoxy)methyl), CHF—SCF₃ (fluoro(trifluorothiomethyl)methyl), and CHF—SC₂F₅ fluoro(pentafluorothioethyl)methyl;

each X is independently selected from the group consisting of F and Cl; and

R¹⁰ and R¹¹ are independently selected from the group consisting of $C_{1-12}$-alkyl, $C_{3-8}$-cycloalkyl, and $C_{7-19}$-arylalkyl,
or
R¹⁰ and R¹¹ are taken together with the nitrogen atom to which they are attached to form a five-membered ring, in the presence of a Lewis Acid with a compound of formula (III)

wherein:
R⁸ is selected from the group consisting of methyl, ethyl, n-propyl, iso-propyl, n-butyl, iso-butyl, sec-butyl, t-butyl, cyclopropyl, cyclobutyl, cyclopentyl, cyclohexyl, phenyl, benzyl, phenylethyl, $C_{7-19}$-alkylaryl, tolyl, 2,3-dimethylphenyl, 2,4-dimethylphenyl, 2,5-dimethylphenyl, 2,6-dimethylphenyl, 3,4-dimethylphenyl and 3,5-dimethylphenyl;
R² is selected from the group consisting of H, F, Cl, Br, COOCH₃, COOC₂H₅, COOC₃H₇, CN, CON(CH₃)₂ and CON(C₂H₅)₂; and
R³ is selected from the group consisting of difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-difluoroethyl, 2,2-dichloro-2-fluoroethyl, 2,2,2-trichloroethyl, tetrafluoroethyl (CF₃CFH), pentafluoroethyl, and 1,1,1-trifluoroprop-2-yl, to form a compound of formula (V-1)

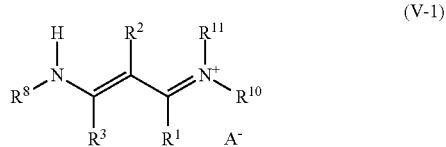

wherein:
A⁻ is $BF_4$, $AlCl_3F$, $AlF_2Cl_2$ or $AlF_3Cl$;
$R^1$ is selected from the group consisting of CHF—$OCF_3$ (fluoro(trifluoromethoxy)methyl), CHF—$OC_2F_5$ (fluoro(pentafluoroethoxy)methyl), CHF—$SCF_3$ (fluoro(trifluorothiomethyl)methyl), and CHF—$SC_2F_5$ fluoro(pentafluorothioethyl)methyl;
$R^2$ is selected from the group consisting of H, F, Cl, Br, $COOCH_3$, $COOC_2H_5$, $COOC_3H_7$, CN, $CON(CH_3)_2$ and $CON(C_2H_5)_2$;
$R^3$ is selected from the group consisting of difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-difluoroethyl, 2,2-dichloro-2-fluoroethyl, 2,2,2-trichloroethyl, tetrafluoroethyl ($CF_3CFH$), pentafluoroethyl, and 1,1,1-trifluoroprop-2-yl;
$R^8$ is selected from the group consisting of methyl, ethyl, n-propyl, iso-propyl, n-butyl, iso-butyl, sec-butyl, t-butyl, cyclopropyl, cyclobutyl, cyclopentyl, cyclohexyl, phenyl, benzyl, phenylethyl, $C_{7-19}$-alkylaryl, tolyl, 2,3-dimethylphenyl, 2,4-dimethylphenyl, 2,5-dimethylphenyl, 2,6-dimethylphenyl, 3,4-dimethylphenyl and 3,5-dimethylphenyl; and
$R^{10}$ and $R^{11}$ are independently selected from the group consisting of $C_{1-12}$-alkyl, $C_{3-8}$-cycloalkyl, and $C_{7-19}$-arylalkyl,
or
$R^{10}$ and $R^{11}$ are taken together with the nitrogen atom to which they are attached to form a five-membered ring,
and step (B), cyclizing the compound of formula (V-1) in the presence of a hydrazine of formula (IV)

 $H_2N$—$NHR^4$ (IV)

wherein:
$R^4$ is selected from the group consisting of H, $C_1$-$C_8$ alkyl, aryl and pyridyl,
to form the compound of formula (Ia) or (Ib).

4. The process according to claim 3, wherein the radicals in formula (Ia), (Ib), (II), (III), (IV), and (V-1) are:
$R^1$ is selected from the group consisting of fluoro(trifluoromethoxy)methyl and fluoro(pentafluoroethoxy)methyl;
$R^2$ is selected from the group consisting of H, Cl, CN and $COOC_2H_5$;
$R^3$ is selected from the group consisting of trifluoromethyl, difluoromethyl, difluorochloromethyl and pentafluoroethyl;
$R^4$ is selected from the group consisting of H, methyl, ethyl, n-propyl, isopropyl, n-butyl, iso-butyl, sec-butyl, t-butyl, n-pentyl, n-hexyl, 1,3-dimethylbutyl, 3,3-dimethylbutyl and aryl;
$R^8$ is selected from the group consisting of methyl, ethyl, n-propyl, iso-propyl, n-butyl, iso-butyl, sec-butyl, t-butyl, cyclopropyl, cyclobutyl, cyclopentyl, cyclohexyl, benzyl and $C_7$-$C_{19}$-alkylaryl;

each X is independently selected from the group consisting of F and Cl; and
$R^{10}$ and $R^{11}$ are independently selected from the group consisting of $C_{1-12}$-alkyl and $C_{3-8}$-cycloalkyl.

5. A process for preparing a 3,5-bis(haloalkyl)pyrazole of formula (Ia) or (Ib)

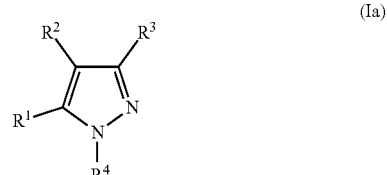

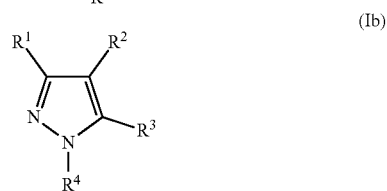

wherein:
$R^1$ is selected from the group consisting of CHF—$OCF_3$ (fluoro(trifluoromethoxy)methyl), CHF—$OC_2F_5$ (fluoro(pentafluoroethoxy)methyl), CHF—$SCF_3$ (fluoro(trifluorothiomethyl)methyl), and CHF—$SC_2F_5$ fluoro(pentafluorothioethyl)methyl;
$R^2$ is selected from the group consisting of H, F, Cl, Br, $COOCH_3$, $COOC_2H_5$, $COOC_3H_7$, CN, $CON(CH_3)_2$ and $CON(C_2H_5)_2$;
$R^3$ is selected from the group consisting of difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-difluoroethyl, 2,2-dichloro-2-fluoroethyl, 2,2,2-trichloroethyl, tetrafluoroethyl ($CF_3CFH$), pentafluoroethyl, and 1,1,1-trifluoroprop-2-yl; and
$R^4$ is selected from the group consisting of H, $C_1$-$C_8$ alkyl, aryl and pyridyl,
comprising: step (A1), reacting an α,α-dihaloalkylamine of formula (II)

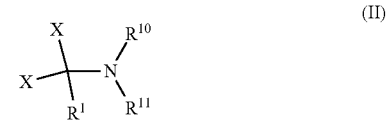

wherein:
$R^1$ is selected from the group consisting of CHF—$OCF_3$ (fluoro(trifluoromethoxy)methyl), CHF—$OC_2F_5$ (fluoro(pentafluoroethoxy)methyl), CHF—$SCF_3$ (fluoro(trifluorothiomethyl)methyl), and CHF—$SC_2F_5$ fluoro(pentafluorothioethyl)methyl;
each X is independently selected from the group consisting of F and Cl; and
$R^{10}$ and $R^{11}$ are independently selected from the group consisting of $C_{1-12}$-alkyl, $C_{3-8}$-cycloalkyl, and $C_{7-19}$-arylalkyl,
or
$R^{10}$ and $R^{11}$ are taken together with the nitrogen atom to which they are attached to form a five-membered ring, in the presence of a Lewis Acid with a compound of formula (III)

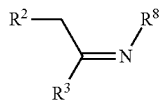
(III)

wherein:
R$^8$ is selected from the group consisting of methyl, ethyl, n-propyl, iso-propyl, n-butyl, iso-butyl, sec-butyl, t-butyl, cyclopropyl, cyclobutyl, cyclopentyl, cyclohexyl, phenyl, benzyl, phenylethyl, C$_{7-19}$-alkylaryl, tolyl, 2,3-dimethylphenyl, 2,4-dimethylphenyl, 2,5-dimethylphenyl, 2,6-dimethylphenyl, 3,4-dimethylphenyl and 3,5-dimethylphenyl;

R$^2$ is selected from the group consisting of H, F, Cl, Br, COOCH$_3$, COOC$_2$H$_5$, COOC$_3$H$_7$, CN, CON(CH$_3$)$_2$ and CON(C$_2$H$_5$)$_2$; and R$^3$ is selected from the group consisting of difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-difluoroethyl, 2,2-dichloro-2-fluoroethyl, 2,2,2-trichloroethyl, tetrafluoroethyl (CF$_3$CFH), pentafluoroethyl, and 1,1,1-trifluoroprop-2-yl, to form a compound of formula (V-1)

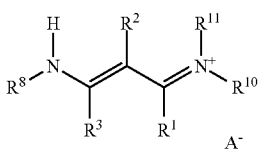
(V-1)

wherein:
A$^-$ is BF$_4$, AlCl$_3$F, AlF$_2$Cl$_2$ or AlF$_3$Cl;

R$^1$ is selected from the group consisting of CHF—OCF$_3$ (fluoro(trifluoromethoxy)methyl), CHF—OC$_2$F$_5$ (fluoro(pentafluoroethoxy)methyl), CHF—SCF$_3$ (fluoro(trifluorothiomethyl)methyl), and CHF—SC$_2$F$_5$ fluoro (pentafluorothioethyl)methyl;

R$^2$ is selected from the group consisting of H, F, Cl, Br, COOCH$_3$, COOC$_2$H$_5$, COOC$_3$H$_7$, CN, CON(CH$_3$)$_2$ and CON(C$_2$H$_5$)$_2$;

R$^3$ is selected from the group consisting of difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-difluoroethyl, 2,2-dichloro-2-fluoroethyl, 2,2,2-trichloroethyl, tetrafluoroethyl (CF$_3$CFH), pentafluoroethyl, and 1,1,1-trifluoroprop-2-yl;

R$^8$ is selected from the group consisting of methyl, ethyl, n-propyl, iso-propyl, n-butyl, iso-butyl, sec-butyl, t-butyl, cyclopropyl, cyclobutyl, cyclopentyl, cyclohexyl, phenyl, benzyl, phenylethyl, C$_{7-19}$-alkylaryl, tolyl, 2,3-dimethylphenyl, 2,4-dimethylphenyl, 2,5-dimethylphenyl, 2,6-dimethylphenyl, 3,4-dimethylphenyl and 3,5-dimethylphenyl; and R$^{10}$ and R$^{11}$ are independently selected from the group consisting of C$_{1-12}$-alkyl, C$_{3-8}$-cycloalkyl, and C$_{7-19}$-arylalkyl, or
R$^{10}$ and R$^{11}$ are taken together with the nitrogen atom to which they are attached to form a five-membered ring, step (A2), reacting the compound of formula (V-1) with water to form a compound of formula (V-2)

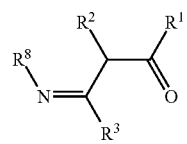
(V-2)

wherein:
R$^1$ is selected from the group consisting of CHF—OCF$_3$ (fluoro(trifluoromethoxy)methyl), CHF—OC$_2$F$_5$ (fluoro(pentafluoroethoxy)methyl), CHF—SCF$_3$ (fluoro(trifluorothiomethyl)methyl), and CHF—SC$_2$F$_5$ fluoro (pentafluorothioethyl)methyl;

R$^2$ is selected from the group consisting of H, F, Cl, Br, COOCH$_3$, COOC$_2$H$_5$, COOC$_3$H$_7$, CN, CON(CH$_3$)$_2$ and CON(C$_2$H$_5$)$_2$;

R$^3$ is selected from the group consisting of difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-difluoroethyl, 2,2-dichloro-2-fluoroethyl, 2,2,2-trichloroethyl, tetrafluoroethyl (CF$_3$CFH), pentafluoroethyl, and 1,1,1-trifluoroprop-2-yl; and R$^8$ is selected from the group consisting of methyl, ethyl, n-propyl, iso-propyl, n-butyl, iso-butyl, sec-butyl, t-butyl, cyclopropyl, cyclobutyl, cyclopentyl, cyclohexyl, phenyl, benzyl, phenylethyl, C$_{7-19}$-alkylaryl, tolyl, 2,3-dimethylphenyl, 2,4-dimethylphenyl, 2,5-dimethylphenyl, 2,6-dimethylphenyl, 3,4-dimethylphenyl and 3,5-dimethylphenyl, and step (B), cyclizing the compound of formula (V-2) in the presence of a hydrazine of formula (IV)

$$H_2N—NHR^4 \qquad (IV)$$

wherein:
R$^4$ is selected from the group consisting of H, C$_1$-C$_8$ alkyl, aryl and pyridyl, to form the compound of formula (Ia) or (Ib).

6. The process according to claim 5,
wherein the radicals in formula (Ia), (Ib), (II), (III), (IV), (V-1) and (V-2) are:

R$^1$ is selected from the group consisting of fluoro(trifluoromethoxy)methyl and fluoro(pentafluoroethoxy)methyl;

R$^2$ is selected from the group consisting of H, Cl, CN and COOC$_2$H$_5$;

R$^3$ is selected from the group consisting of trifluoromethyl, difluoromethyl, difluorochloromethyl and pentafluoroethyl;

R$^4$ is selected from the group consisting of H, methyl, ethyl, n-propyl, isopropyl, n-butyl, iso-butyl, sec-butyl, t-butyl, n-pentyl, n-hexyl, 1,3-dimethylbutyl, 3,3-dimethylbutyl and aryl;

R$^8$ is selected from the group consisting of methyl, ethyl, n-propyl, iso-propyl, n-butyl, iso-butyl, sec-butyl, t-butyl, cyclopropyl, cyclobutyl, cyclopentyl, cyclohexyl, benzyl and C$_7$-C$_{19}$-alkylaryl;

each X is independently selected from the group consisting of F and Cl; and $R^{10}$ and $R^{11}$ are independently selected from the group consisting of $C_{1-12}$-alkyl and $C_{3-8}$-cycloalkyl.

* * * * *